United States Patent [19]

Green

[11] Patent Number: 4,699,998

[45] Date of Patent: Oct. 13, 1987

[54] PROCESS FOR THE PREPARATION OF GLYCOL DERIVATIVES

[75] Inventor: Michael J. Green, Hedon, England

[73] Assignee: BP Chemicals Limited, London, England

[21] Appl. No.: 646,961

[22] Filed: Sep. 4, 1984

[30] Foreign Application Priority Data

Sep. 7, 1983 [GB] United Kingdom ............... 8323962

[51] Int. Cl.$^4$ ............................................. C07C 67/24
[52] U.S. Cl. ................................. 560/240; 560/182; 560/199; 560/200; 560/263; 568/678; 260/410.6
[58] Field of Search ............... 560/182, 200, 240, 263, 560/199, 263; 568/678; 260/410.6

[56] References Cited

FOREIGN PATENT DOCUMENTS 44-18845  8/1969  Japan ................................... 560/240

Primary Examiner—Werren B. Lone
Attorney, Agent, or Firm—Brooks Haidt Haffner & Delahunty

[57] ABSTRACT

Glycol ether esters can be prepared by reaction of an epoxide with an ester of a carboxylic acid using an amidine catalyst. The reaction can be used, for example, to prepare methoxypropyl acetate propylene oxide and methyl acetate. By carrying the reaction out in the presence of an alcohol solvent the corresponding glycol ether is also formed.

17 Claims, No Drawings

PROCESS FOR THE PREPARATION OF GLYCOL DERIVATIVES

This invention relates to a process for the preparation of compounds containing an ether linkage and an ester group hereafter referred to as glycol ether esters and the optional coproduction of compounds containing an ether linkage and a hydroxyl group hereafter referred to as glycol ethers.

The preparation of glycol ether esters has been described in German Offenlegenschrift No. 2,951,080 which proposes the production of an alkylene glycol ether carboxylate by reaction of an alkylene glycol and a carboxylate ester using a zirconium halide catalyst with a cocatalyst chosen from benzotriazoles, N-alkyl amides, N-alkyl pyrrolidones and primary, secondary and tertiary amines.

It is an object of the present invention to provide a catalytic system for the preparation of glycol ether esters which is soluble in the reaction mixture and is non-corrosive.

According to the present invention a process for the preparation of glycol ether esters comprises reacting an epoxide with an ester of a carboxylic acid using, as catalyst, an effective amount of an amidine.

By amidine is meant a compound containing the grouping:

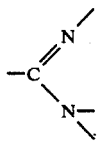

Conveniently the free valencies on the nitrogen atoms are attached to carbon atoms or hydrogen and the free valency on the carbon atom to another carbon atom or nitrogen atom. In the last mentioned case the structure will comprise a guanidine grouping e.g., a cyclic guanidine.

The amidine group-containing compound can be cyclic or acyclic. The amidine group can be directly attached to a ring or form part of a heterocyclic ring in particular a fused ring system. For example the amidine can be 1,5-diazabicyclo[4.3.0]non-5-ene of formula:

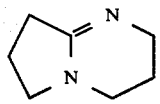

or 1,8-diazabicyclo[5.4.0]undec-7-ene of formula:

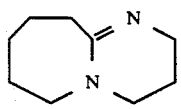

or 1,5,7-triazabicyclo[4.4.0]dec-5-ene of formula

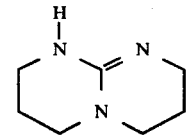

Suitable amounts of the amidine catalyst are from 0.001 to 10 preferably from 0.01 to 5% by wt of the total reaction mixture.

Although any ester of a carboxylic acid can be used, the ester is conveniently a $C_1$ to $C_6$ alkyl ester of a $C_1$ to $C_6$ carboxylic acid. The acid may be a monocarboxylic acid, e.g. acetic acid or a dicarboxylic acid e.g. maleic acid, tartaric acid. Preferred esters are the methyl and ethyl esters of a $C_1$ to $C_6$ aliphatic carboxylic acid of which the methyl and ethyl esters of acetic, propionic and butanoic acids are most preferred.

The reaction can be carried out in the presence of an alcohol in which case the corresponding glycol ether is also formed. The alcohol can conveniently be for example methanol, ethanol, butanol, phenol or allyl alcohol.

The epoxide can be a compound of the formula

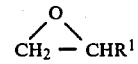

where $R^1$ is hydrogen or a monovalent aliphatic group which may conveniently contain from 1 to 6 carbon atoms such as ethylene, propylene and butylene oxides.

Conveniently a molar excess of ester is employed when the objective of the process is to produce a monoglycol ether ester. A suitable range of molar ratios of the ester of the carboxylic acid to epoxide is from 1:1 to 10:1. The molar ratio of the carboxylic acid to the epoxide may be from 2:1 to 10:1.

When the objective is to prepare a polyglycol ether ester however a molar excess of epoxide should be used. The molar ratio of the ester of the carboxylic acid to the epoxide should then be from 1:1 to 1:10. The glycol ether ester may be an adduct of one molecule of the ester of the carboxylic acid and two or more molecules of the epoxide.

The reaction can be carried out at ambient temperature but is conveniently carried out at elevated temperature in order to increase the rate of reaction. The temperature of reaction should suitably be in the range 40° to 200° C. with the range 70° to 130° C. being the most preferable.

As regards pressure this should be in the range 1 to 300 psi, preferably 1 to 150 psi. In most cases it is convenient to operate the process at a pressure corresponding to the autogenous pressure of the reactants at the temperature of reaction.

The reaction may be carried out batchwise or continuously.

The invention is illustrated by the following examples.

EXAMPLE 1

A Fischer-Porter tube was charged with 10 g of propylene oxide, 35 g of methyl acetate, 1.75 g of methanol, and 0.5 g of 1,5,7-triazabicyclo[4.4.0]dec-5-ene (TBD). The tube was purged with nitrogen to remove air, pressurised to 100 psi with nitrogen, sealed, and finally heated to 120° C. with stirring. After 2 hours the tube was cooled and depressurised. Analysis of the liquid product by gas chromatography showed an 89% conversion of propylene oxide with a 56% selectivity to methoxypropyl acetate and a 30% selectivity to methoxypropanol. Small amounts of the corresponding 2:1 adducts were also formed.

EXAMPLE 2

Example 1 was repeated in the presence of 0.5 g methanol. Analysis of the liquid product showed an 82% conversion of propylene oxide with a 60% selectivity to methoxypropylacetate and a 23% selectivity to methoxypropanol.

EXAMPLE 3

Example 1 was repeated in the absence of methanol. Analysis of the liquid product showed a 75% conversion of propylene oxide with a 60% selectivity to methoxypropyl acetate and an 11% selectivity to the 2:1 propylene oxide:methyl acetate adduct.

EXAMPLE 4

Example 1 was repeated except that the Fischer-Porter tube was charged with 17.5 g of ethyl acetate, 5 g of propylene oxide, 1 g of ethanol and 0.25 g of TBD. Analysis of the liquid product showed a 93% conversion of propylene oxide with a 54% selectivity to ethoxypropyl acetate and a 29% selectivity to ethoxypropanol. Small amounts of the corresponding 2:1 adducts were also formed.

EXAMPLE 5

Example 1 was repeated except that 10 g of butylene oxide was used in place of propylene oxide. Analysis of the liquid product showed a 56% conversion of butylene oxide with a 48% selectivity to methoxybutyl acetate and a 52% selectivity to methoxybutanol.

EXAMPLE 6

Example 4 was repeated except that 17.5 g of methyl propionate was used in place of ethyl acetate. Analysis of the liquid product showed a 93% conversion of propylene oxide with a 46% selectivity to methoxypropyl propionate and a 42% selectivity to methoxypropanol. Small amounts of the corresponding 2:1 adducts were also formed.

COMPARATIVE EXAMPLE A

Example 1 was repeated in the absence of TBD. Analysis of the liquid product indicated that no reaction had taken place.

I claim:

1. A process for the preparation of a mono- or polyglycol ether ester which process comprises reacting an epoxide of the formula

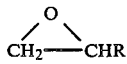

where R is hydrogen or a monovalent aliphatic group having from 1 to 6 carbon atoms with an ester of a carboxylic acid in the presence of an effective amount of a catalyst characterised in that the catalyst is an amidine.

2. A process as claimed in claim 1 characterised in that the amidine is a cyclic amidine.

3. A process as claimed in claim 1 characterised in that the amidine is a guanidine.

4. A process as claimed in claim 3 characterised in that the guanidine is a cyclic guanidine.

5. A process as claimed in claim 1 characterised in that the glycol ether ester is an adduct of one molecule of the ester of the carboxylic acid and one molecule of the epoxide.

6. A process as claimed in claim 5 characterised in that the molar ratio of the ester of the carboxylic acid to the epoxide is from 2:1 to 10:1.

7. A process as claimed in claim 1 characterised in that the glycol ether ester is an adduct of one molecule of the ester of the carboxylic acid and two or more molecules of the epoxide.

8. A process as claimed in claim 1 characterised in that the reaction is carried out in the presence of an alcohol and the corresponding glycol ether is coproduced.

9. The process as claimed in claim 1, wherein said catalyst is 1,5-diazabicyclo[4.3.0]non-5-ene.

10. The process as claimed in claim 1, wherein said catalyst is 1,8-diazabicyclo[5.4.0]undec-7-ene.

11. The process as claimed in claim 1, wherein said catalyst is 1,5,7-triazabicyclo[4.4.0]dec-5-ene.

12. A process for the preparation of a glycol ether ester which process comprises reacting an epoxide of the formula

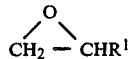

where $R^1$ is hydrogen or a monovalent aliphatic group having from 1 to 6 carbon atoms,
  with an ester of a carboxylic acid, which is a $C_1$ to $C_6$ alkyl ester of a $C_1$ to $C_6$ aliphatic monocarboxylic acid or a $C_1$ to $C_6$ aliphatic dicarboxylic acid,
  in the presence of an effective amount of a catalyst selected from the group consisting of 1,5-diazabicyclo[4.3.0]non-5-ene, 1,8-diazabicyclo[5.4.0]undec-7-ene, and 1,5,7-triazabicyclo[4.4.0]dec-5-ene,
  wherein said effective amount of the catalyst is from 0.001 to 10% by weight of the total reaction mixture.

13. The process as claimed in claim 12, wherein said effective amount of said catalyst is from 0.01 to 5% by weight of the total reaction mixture.

14. The process as claimed in claim 12, wherein said epoxide is selected from the group consisting of ethylene oxide, propylene oxide and butylene oxide.

15. The process as claimed in claim 12 wherein said ester is selected from the group consisting of a methyl or ethyl ester of acetic acid, propionic acid, butanoic acid, maleic acid and tartaric acid.

16. The process as claimed in claim 12,
  wherein said epoxide is propylene oxide or butylene oxide,
  wherein said ester is methyl acetate, ethyl acetate, or methyl propionate, and
  wherein said catalyst is 1,5,7-triazabicyclo[4.4.0]dec-5-ene.

17. The process as claimed in claim 12, wherein the reaction is carried out in the presence of an alcohol selected from the group consisting of methanol, ethanol, butanol, phenol and allyl alcohol,
  and the corresponding glycol ether is coproduced.

* * * * *

UNITED STATES PATENT AND TRADEMARK OFFICE
CERTIFICATE OF CORRECTION

PATENT NO. :   4,699,998

DATED      :   October 13, 1987

INVENTOR(S) :  Michael James Green

It is certified that error appears in the above-identified patent and that said Letters Patent is hereby corrected as shown below:

Title page under heading ABSTRACT, line 4
"to prepare methoxypropyl acetate propylene" should read
-- to prepare methoxypropyl acetate from propylene --

Signed and Sealed this

Twelfth Day of April, 1988

Attest:

DONALD J. QUIGG

Attesting Officer

Commissioner of Patents and Trademarks